(12) United States Patent
Park et al.

(10) Patent No.: US 7,449,498 B2
(45) Date of Patent: Nov. 11, 2008

(54) COMPOSITE MATERIALS FOR BONE DEFECT FILLING AND BONE REPLACEMENT

(75) Inventors: Kyeong-Jun Park, Goyang-si (KR); Doug-Youn Lee, Goyang-si (KR); Sang-Bae Lee, Goyang-si (KR); Jeong-Jong Park, Goyang-si (KR); Ji-Ho Park, Seoul (KR); Kyoung-Nam Kim, Seoul (KR); Kwang-Mahn Kim, Seoul (KR)

(73) Assignee: Yesbio Co., Ltd., Goyang-Si (KR)

( * ) Notice: Subject to any disclaimer, the term of this patent is extended or adjusted under 35 U.S.C. 154(b) by 245 days.

(21) Appl. No.: 11/296,944

(22) Filed: Dec. 8, 2005

(65) Prior Publication Data
US 2006/0276562 A1    Dec. 7, 2006

(30) Foreign Application Priority Data
Jun. 4, 2005    (KR) .................... 10-2005-0048061

(51) Int. Cl.
*A61F 2/28* (2006.01)
*C08K 9/04* (2006.01)
*C08K 3/32* (2006.01)

(52) U.S. Cl. .................. 523/115; 523/116; 523/202; 524/414

(58) Field of Classification Search .............. 523/116, 523/202, 115; 524/414
See application file for complete search history.

(56) References Cited

U.S. PATENT DOCUMENTS 4,192,021 A * 3/1980 Deibig et al. ............ 623/23.61
5,874,509 A * 2/1999 Shalaby et al. .............. 526/194
2005/0283255 A1* 12/2005 Geremakis et al. ....... 623/23.51
2006/0210598 A1* 9/2006 Evans et al. ................ 424/422
2007/0088437 A1* 4/2007 Betz et al. ................ 623/17.11

OTHER PUBLICATIONS

Park et al, Bioactive Cyanoacrylate-based Filling Material for Bone Defects in Dental Applications in Bioceramics, vol. 17, Proceedings of the 17th International Symposium on Ceramics in Medicine, New Orleands, Louissiana, U.S.A., Dec. 8-12, 2004.*
Park et al., "Bioactive Cyanoacrylate-based Filling Material for Bone Defects in Dental Applications," Key Engineering Materials vol. 284-286:933-936, 2005.

* cited by examiner

*Primary Examiner*—Tae H Yoon
(74) *Attorney, Agent, or Firm*—Clark & Elbing LLP (57) ABSTRACT

The present invention relates to composite materials for bone replacement comprising organic and inorganic material, more particularly to composite materials for bone replacement wherein cyanoacrylate as organic material and osteoconductive inorganic material as inorganic material are combined. The composite materials synthesized according to the present invention, maximize the merits of organic material and inorganic material and minimize their demerits. In detail, the organic material has the maintenance of shape and the adhesive property and the inorganic material has the osteoconductivity on a new bone. Therefore, the composite materials of the present invention can be applied to fill bone defects and replace bones, since they retain the excellent physical property.

6 Claims, 11 Drawing Sheets
(7 of 11 Drawing Sheet(s) Filed in Color)

COMPOSITE MATERIALS FOR BONE DEFECT FILLING AND BONE REPLACEMENT

CROSS REFERENCE TO RELATED APPLICATION

This application is based on, and claims priority to Korean Patent Application No. 10-2005-0048061, filed on Jun. 4, 2005, the disclosure of which is hereby incorporated by reference.

BACKGROUND OF THE INVENTION

1. Field of the Invention

The present invention relates to composite materials for bone defect filling and bone replacement comprising organic material and inorganic material, more particularly to composite materials for bone defect filling and bone replacement wherein cyanoacrylate as organic material and bioactive osteo-conductive inorganic material as inorganic material are combined.

2. Description of the Related Art

Bone researches are investigated a lot in overall medical fields including dentistry and orthopedic surgery. Materials for bone replacement should have excellent tissue compatibility, be available in unlimited quantities, be easy contoured, retain stable shape over time, become ingrowth or replaced by living tissue. However, there is no material suitable for this use yet.

Presently, the bone replacement is conducted merely by implanting an autograft in a lesion lacking in bones. The bone autograft is most outstanding to bone regeneration. But, after operating the autograft, the prognosis is discriminated, depending upon lesion sites. That is to say, the autograft may not demonstrate its function properly due to histological differences in between donor site and acceptor site. Furthermore, the autograft is limited in the amount, if needed a lot. This operation may overburden on both the patient and manipulators, if repeated.

In order to find out another materials for implanting an autograft-like bone, allogenic or xenogenic bones are selected. The allograft or xenograft are not produced easily and may cause a histological rejection either. Therefore, bone researches start to investigate alloplastic bones or synthetic bones. For this purpose, almost all materials such as metal, organic material and ceramic are being examined, but not applied satisfactorily yet.

In detail, the metal refers to an implant using pure titanium alloy etc. The implant alloy is utilized to replace roots of teeth and plays a partial function of bone. However, this is limitedly used, when osseous injuries are less dense or wide. Thus, the metal alloy is still considered unsuccessful, because it cannot replace bones directly. Further, the metal alloy is lacking in sustaining the original shape of bone.

In addition, the organic material exemplifies polymethyl methacrylate (PMMA). However, the PMMA is problematic to cause cell necrosis because of polymerization heat and toxicity of monomer. Further, the organic material may cause the isolation of implant metals and adverse actions like a foreign body, if used for a long time, because it is hardly absorbed and replaced by bone. Vale, Vazquez, Vila and their collaborators have investigated to minimize the harmfulness, when the bone implant and adhesive material are used on a hip joint. Besides, Kawanabe has attempted to apply Bis-GMA (2,2-bis[4-(2-hydroxy-3-methacryloyloxypropoxy) phenyl] propane) into bones. However, this study regarded bone adhesive material, like PMMAs either. In the plastic surgery, the PMMA is used to connect metals for replacing a hip joint to bones.

In addition, the inorganic material similar to the inorganic constituent of bones is cited. Brown et al. have examined porous hydroxyapatite (HA) for an absorbable inorganic material. Wolfe has elucidated that β-tricalcium phosphate (β-TCP) is degraded slowly so as to be replaced by new bones, since it has the same structure with the inorganic component of natural bone. Chow et al. have reported the osteo-conductivity of β-TCP. Also, Possets et al. have disclosed researches on tetracalcium phosphate and Frankenburg et al. have published studies on calcium phosphate cement and the like. In addition to simple bone cements, the bone cement mixture blending several inorganic materials, is investigated to be manufactured. This bone cement is made of viscous substance excluding a powered form to reduce the initial fluidity and maintains the shape in some extent. However, the result is not expected to satisfy all the needs. Most materials are often provided in a powder or have insufficient strength to be molded. Thus, their molding is hardly maintained and restricts the availability on lesion sites operated. Furthermore, the scaffold block used for implant is not easily manipulated to be adapted on a lesion.

These bioactive ceramic materials for bone regeneration described above are not osteo-inductive but osteo-conductive. Therefore, these ceramic materials are preferred to have a porous body containing proper pores connected and be permeated by bone tissue according to the growth. Further, they are required to adjust the biodegradation similar to the growth of new bones in their speeds. However, β-TCP is disadvantageous because it is to be utilized either in a powder or in a scaffold block reducing its strength.

Finally, the composite material combining inorganic material and organic material is being described. Raveh et al. have investigated to manufacture the composite material by using bioglass and Bis-GMA(2,2-bis[4(2-hydroxy-3-methacryloxypropoxy) phenyl]propane). However, this composite material is not absorbed completely and brings about adverse actions after operated. Especially, it is recognized as a foreign body due to lacking in adhesiveness. In addition, Wright et al. have contrived to prepare a composite material by mixing reinforcing fiber and PMMA. This composite material may disperse the heat of polymerization from PMMAs to prevent bone necrosis during the reaction. Nevertheless, this material has a too low adhesive strength as a glue to be applied actively. Mostly, these composite materials adopted non-absorbable substance and combined PMMAs matrix with inorganic material in order to improve the thermal property or resist during being cut. Commonly, the inorganic material is added in a ratio of 10 to 20%. Furthermore, Bank et al. started to synthesize composite materials by using hydroxyapatite (HA) and collagen and then, continue to manufacture the composite material by using HA and fibrin.

In order to settle above-mentioned problems, the present inventors have tried to prepare composite materials that maximize the merits of inorganic material and organic material and minimize their demerits. As a consequence, we have manufactured novel materials excellent in the physical property for bone replacement and bone defect filling, because the organic material has the maintenance of shape and the adhesive property and the bioactive inorganic material has the osteo-conductivity on new bones and completed the present invention successfully as follows.

SUMMARY OF THE INVENTION

The object of the present invention is to provide composite materials for bone replacement excellent in the physical property that maximize the merits of inorganic material and organic material and minimize their demerits.

In order to attain the above-mentioned objects, the present invention provides composite materials for bone defect filling and bone replacement that combine organic material and inorganic material, wherein the organic material is cyanoacrylate and the inorganic material is osteo-conductive inorganic material modified on the surface by using inhibitors against the polymerization of the organic material.

In the composite materials of the present invention, the cyanoacrylate is an organic substance commonly known as an instant adhesive agent and polymerized rapidly when hydroxyl (—OH) groups exist around. Conventionally, the cyanoacrylate is hardly molded, since polymerized immediately after contacting with inorganic substances. Preferably, the cyanoacrylate can be n-butyl-2-cyanoacrylate(BCA) and octyl-cyanoacrylate. The n-butyl-2-cyanoacrylate is less toxic and the octyl-cyanoacrylate is already approved by FDA.

In the composite materials of the present invention, the osteo-conductive inorganic material refers to inorganic material that is absorbed or remains within a living body to conduct and regenerate bones. Preferably, the inorganic material can be selected from a group comprising Hydroxyapatite (HA: $Ca_{10}(PO_4)_6(OH)_2$), calcium phosphate cements, calcium carbonate, calcium sulfate (calcium sulfate+TCP), tricalcium phosphate (TCP), Bioplast HTR, bioactive glass ceramic, silica and the like, but not limited within the group. More preferably, the inorganic material can be the calcium phosphate selected among $\alpha,\beta$-tricalcium phosphate, dicalcium phosphate dibasic, tetracalcium phosphat and most preferably, $\beta$-tricalcium phosphate.

In the composite materials of the present invention, the osteo-conductive inorganic material is modified on the surface to encapsulate hydroxyl groups stimulating the polymerization of cyanoacrylate by using proper inhibitors against the polymerization. The polymerization inhibitor can be any substance retarding the reaction by adjusting the acidity or by blocking on the surface of the inorganic material or by affecting the polymerization. Preferably, the inhibitor can be selected among acidic inhibitors, free radical inhibitors, polymers non-reactive with cyanoacrylate or the like. More preferably, the inorganic material can be encapsulated on the surface by acids and by polymers. The acids can be any acids, if non-toxic to a human body and preferably, citric acid. In addition, the polymers can be any bio-degradable polymers. Preferably, the polymers can be selected from a group comprising dextrin, corn starch, polycarprolactone, polylactide, polyglycolide, poly(lactide-co-glycolide) and their copolymers and more, preferably, dextrin.

In the composite materials of the present invention, the cyanoarylate and the osteo-conductive inorganic material can be combined in any ratios, if advantageous. Preferably, the ratio of combination can be in the range of 1:4 to 1:7. Within this ratio range, the composite materials have the excellent physical properties including absorption, solubility, and compressive strength.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

DETAILED DESCRIPTION OF THE INVENTION

Hereinafter, the present invention will be described more clearly as follows.

First, all the materials used for the composite material of the present invention are selected from bioabsorbable materials. Especially, $\beta$-TCP is selected for an inorganic material, since absorbable and most actively investigated. In addition, n-butyl-2-cyanoacrylate (BCA) is selected for an organic material since it has proper physical properties and biodegradabiliy.

$\beta$-TCP has investigated a lot to develop implant materials for synthetic bones. $\beta$-TCP has the chemical composition similar to that of natural bones and the bio-compatibility excellent with a living body. As reference, $\beta$-TCP is reported to make a bone-like apatite on the interface between bone tissue and material, after implanted. Thus, $\beta$-TCP may be combined directly or indirectly with the osseous tissue.

Preferably, this bio-ceramic material for bone replacement can be a porous body (scaffold). This porous body contains pores having a proper size and connected to be permeated by osseous tissue. Further, it should have the bio-degradation rate similar to the growth rate of new bones. However, $\beta$-TCP has been used only in a powder form or in a scaffold block with low strength. Resultantly, β-TCP requires matrix materials to prevent the movement and to increase the strength.

Cyanoacrylate (CA) was conventionally known as an instant adhesive. CA can be utilized widely on both hard and soft tissues, due to the rapidity of adhesiveness in the presence of water. It is toxic, especially carcinogenic, but the toxicity reduces gradually if elongating its side chain to C3 to 8. In practice, less toxic n-butyl-2-cyanoacrylate (BCA) is commercially available as a product name Histoacryl® and the like and substitutes suture threads for adhering soft tissues. The BCA is weakly cytotoxic, but applied widely as an adhesive agent for soft tissue, because it is bacteriostatic, conveniently handled and coagulate blood rapidly. Recently, BCA is being intensely studied by Amarante and Shermak et al. and tends to raise its effective values. In the composite materials of present invention, less toxic n-butyl-2-cyanoacrylate (BCA) is selected and applied as described in Examples.

Sole BCA cannot be utilized for bone replacement material. If mixed with inorganic material such as HA or TCP, BCA can reduce the toxicity, increase the bio-compatibility, be combined mechanically between inorganic materials and stimulate the osteogenesis. It is reported that β-TCP degraded slowly to replace the empty space by new bone, due to the structural similarity to inorganic components of bone.

Traditionally, it is almost impossible to mix BCA and β-tricalcium phosphate. The reason can be easily understood by the polymerization mechanism of cyanoacrylate. Practically, cyanoacrylate can polymerize at room temperature without catalyst, heating, pressure and removing solvent. That is to say, the cyanoacrylate is often used as an instant adhesive agent and especially, brings about an ionic polymerization right after exposed in the air. In detail, CA reacts momentarily when adding a weak base and polymerized. This reaction can proceed rapidly, when moisture as a weak base exists.

β-TCP is weakly basic in pH 7.2 to 7.5. β-TCP often contain a certain amount of moisture even in a powder to decrease its weight by approximately 5%, when dried by heating at 120° C. for 4 hours. For this reason, it is not possible to mix β-TCP and CA simply.

Therefore, the present inventors have attempted to find out novel methods for mixing β-TCP with CA without chemical modification. First, β-TCP is encapsulated with other biodegradable polymers on the surface in order to facilitate their combination, even maintaining its physical property. Second, β-TCP is encapsulated on the surface with acids to be neutralized or acidified, since its surface is weakly basic. This procedure makes these materials combined easily without additional components.

In the composite materials of the present invention, the osteo-conductive inorganic material is modified on the surface to encapsulate hydroxyl groups stimulating the polymerization of cyanoacrylate by using a proper inhibitor against the polymerization. The polymerization inhibitor can be any substance retarding the reaction by adjusting the acidity on the surface of the inorganic material or by blocking or by affecting the polymerization negatively. Preferably, the inhibitor can be selected among acidic inhibitors, free radical inhibitors, polymers non-reactive with cyanoacrylate or the like. More preferably, the inorganic material can be encapsulated on the surface by treating acids and by coating polymers. The acids treated above can be any acids, if non-toxic to a living body and preferably, citric acid. In addition, the polymers coated above can be any bio-degradable polymers. Preferably, the polymers can be selected from a group comprising dextrin, corn starch, polycarprolactone, polylactide, polyglycolide, poly(lactide-co-glycolide) and their copolymers and more, preferably, dextrin.

In Examples of the present invention, Histoacryl, a commercially available BCA is utilized. The Histoacryl is a tissue adhesive and mainly composed of monomeric n-butyl-2-cyanoacrylate. The tissue adhesive using CA base material consists in various kinds such as SYC, Dermabond, Traumaseal and GluStitch. In spite of the kinds, the tissue adhesive is seldom adopted for osseous use. Pure BCA should be mixed with polymers due to its very low viscosity in order to combine coarse tissues like bone. However, the polymers affect the physical property such as adhesiveness badly. Further, pure BCA may bring about cell necrosis due to its high heat of reaction.

Sole use of BCA is restricted for bone replacement material. If mixed with HA or β-TCP, BCA can bind bones and inorganic material mechanically and stimulate the osteogenesis. The β-TCP added reduces the toxicity of BCA and enhances the bio-compatibility. In order to achieve this effect, β-TCP is required to retain a predetermined strength and not to move within a living body. Further, a mixture of BCA and β-TCP has the viscosity sufficient to stick bones and can degrade without adverse action.

Figure 2:
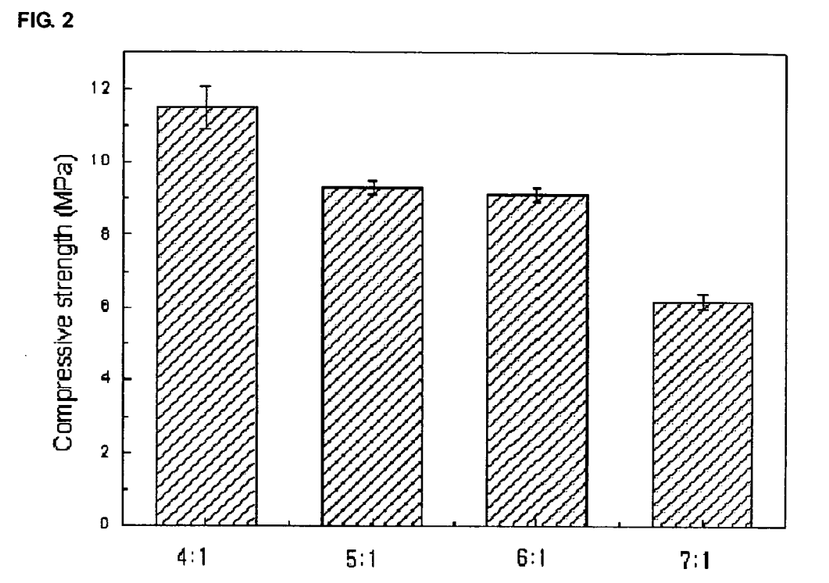
FIG. 2 depicts the compressive strength according to combination ratios in the composite material of the present invention.

In the composite materials of the present invention, the compressive strength after combination becomes higher to reach approximately 10 MPa, as the content of Histoacryl increases to fortify the adhesive strength (See FIG. 2). As reference, ordinary inorganic scaffolds have approximately 5 MPa of the strength similar to cancellous bones, even if outstanding it is concluded that the morphology of bones may be retained under an applied pressure after initial hardening due to such an excellent strength. The composite materials of the present invention may prevent the movement of teeth and regenerate tooth sockets, when filled around patient's teeth suffering from severe periodontal cystis. Further, it is deduced that the patient may chew early after operation. Therefore, it is confirmed that the composite material for bone defect filling and bone replacement of the present invention illustrated more excellent results than any other materials. Further, it may endure chewing actions early due to the adhesive strength, as examined in the preliminary experiment. Hence, the composite material for bone defect filling and bone replacement of the present invention may act simply right after implanted, depending upon advanced results.

In the exothermic aspect, sole Histoacryl increases the temperature due to the polymerization heat by approximately 4° C. during suturing soft tissues. In contrast, the composite materials of the present invention increase the temperature less by approximately 3° C. (0.7 to 3.5° C.) even if varying according to ratios and thus, reduces the risk of tissue necrosis (See FIG. 3). In this study, Histoacryl itself increased the temperature by approximately 15° C. and rather resulted in a higher value. At this moment, Histoacryl is mixed with a small amount of pure β-TCP, since it is not polymerized easily in a large amount. As a result, the inorganic material is proved to disperse heat effectively, in spite of simple comparison. In detail, the addition of β-TCP reduces the amount of Histoacryl used relatively. Therefore, this material can be applied for an adhesive agent and substitute PMMA bone cement in the future, if reducing the heat of polymerization and improving the adhesive strength.

In the cytotoxic aspect, Histoacryl appears moderately toxic. As disclosed, n-butyl-cyanoacrylate is initially inflammatory within tissues for several weeks, but biocompatible to recover a normal condition of tissue fast. Presently, only octyl-cyanoacrylate has approved by FDA. Therefore, the composite materials using thereof need to be investigated in advance. As reference, β-TCP tends to have a higher biocompatibility, due to the composition and structure similar to bones. As described in experiments, when β-TCP added more in the composition, the toxicity of composite decreases.

The absorption and the solubility of the composite materials should be maintained in fixed levels. If degrading too fast, the material for bone replacement may fall apart in a powder before osteogensis and arouse adverse reactions of foreign bodies as time lapses, even if sustaining the original shape. Further, if not dissolved and degraded at all, the material may not acquire proper space substituted by bones in spite of the excellent bone replacement. In order to absorb the material, the space for filling body fluid should be reserved and further, the body fluid filled within the space facilitates the osteoconductance. That is to say, the composite materials should be dissolved in order to substitute bones. According to the experimental result, if β-TCP is more added, the composite material is more absorbed and dissolved.

In the process for attaching cells or other material on the surface, the surface energy is often important. In order to increase the surface energy, the surface is treated coarse. This process may enhance the surface energy naturally. In detail, the composite materials are examined for 12 weeks to observe the changed within simulated body fluid (hereinafter, referred to as "SBF"). The resulting material is identified to roughen the surface by being dissolved. Also, HA is observed to help osteogenesis after synthesized, under 50,000× of magnification. Therefore, the composite materials of the present invention are clarified to satisfy all the conditions suitable for the osteogenesis.

In the ideal implants, the osseous lesions filled with certain material is preferred to be replaced by new bones, while the material is degraded gradually. If possible, the material is more preferred not to change the shape early and maintain the original shape and function for a time period.

As described in the experiment of the present invention, the control group left injured without any manipulation is observed to fill the lesion site with connective tissues out of a margin portion. Any regeneration by the action of periosteum is not detected. The experimental group implanted with autografts is observed to regenerate bones without any toxicity, rejection or inflammation. But the broken bone powders are not combined each other and filled with connective tissue after 8 weeks. The experimental group filled with the composite material directly on osseous lesion is not permeated by connective tissues, excluding the TCP or BCA space and maintains the shape well. The result is almost comparable to that of the autograft group. The autograft can maintain the original shape by excluding mechanical stimuli. In contrast, the synthetic composite materials can maintain the original shape excellently even under an intact condition. For this reason, it is deduced to regenerate bones without any adverse action of foreign bodies.

The experimental group treating a round plate-type implant is observed to make new bones actively on osseous lesions contacting the material, as the experimental group for augmentation does. By performing SBF precipitation and XRD examination, this reaction is elucidated to be caused by the osteo-conductance of HA rather than by the induction of periosteum. After 16 weeks, the round plate-type implant changes to appear irregular and includes new bones over and beneath the implant. As a consequence, it is confirmed that compact composite material itself may be degraded or absorbed to replace bones after more than 3 months. Therefore, the composite materials of the present invention matches several processes harmoniously such as osteogenesis, degradation of BCA matrix and the absorption of β-TCP and excludes the mobility by using BCA without the adverse action of foreign bodies.

Practical and presently preferred embodiments of the present invention are illustrated as shown in the following Examples.

However, it will be appreciated that those skilled in the art, on consideration of this disclosure, may make modifications and improvements within the spirit and scope of the present invention.

EXAMPLE 1

Preparation of BCA and β-TCP Composite

A. Acid Treatment of Inorganic Material

In order to delay the reaction while preparing composite material, β-TCP (Fluka Chemie, GmbH, Switzerland) was treated with citric acid (Aldrich Chemical Co., U.S.A). 0.1 g of citric acid was dissolved in 100 ml of distilled water and deposited with 20 g of β-TCP. After 24 hours, the resultant was centrifuged at 1,500 rpm and dried at 50° C. for 12 hours to treat the surface.

B. Encapsulation of Inorganic Material by Using Biodegradable Polymer

In order to delay the reaction while preparing composite material, β-TCP was encapsulated with dextrin (Aldrich Chemical Co., U.S.A). 5 g of dextrin was dissolved with 30 9 of water and stirred at 80° C. for an hour. Then, 15 g of β-TCP was added and dispersed in the resulting dextrin solution. As maintaining a temperature, ethyl alcohol was added slowly in an excess amount to the suspension prepared above to precipitate dextrin for encapsulating β-TCP. As decreasing a temperature and stopping to stir, β-TCP encapsulated with dextrin was soaked to remove the supernatant and dried at 50° C. in an oven for 12 hours to proceed the next step.

C. Preparation of Composite Material

Histoacryl (Aesculap Ag & Co. Kg, Tuttingen/Germany) and β-TCP treated with an acid were mixed in a weight ratio of 1:4 (75%), 1:5 (80%), 1:6 (83.3%), 1:7 (85.7%) respectively as illustrated in Table 1 to prepare composite material. The composite material was made to have a uniform viscosity similar to the sample in a powder and liquid state by using paper and a plastic device. At this moment, the reaction was proceeded at a low humidity since it is sensitive to moisture.

Figure 1:
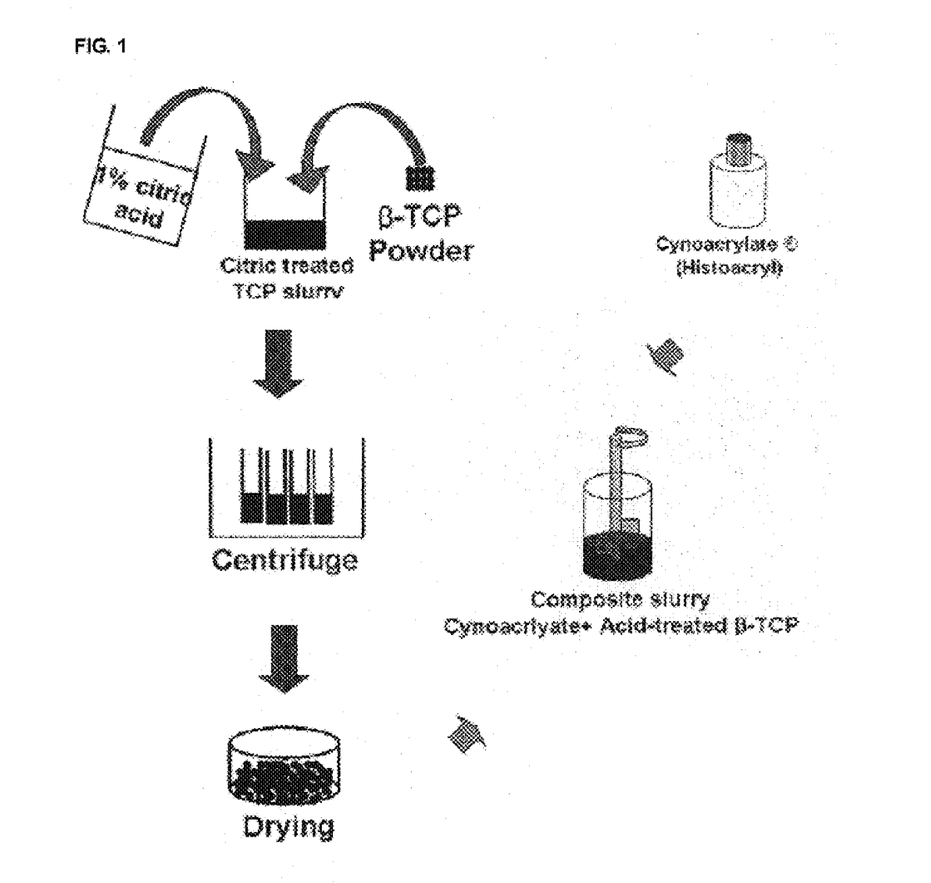
FIG. 1 depicts the overall view of the process for preparing the composite material of BCA and $\beta$-TCP.

FIG. 1 depicts the overall view of the process for preparing the composite materials of BCA and β-TCP.

TABLE 1

| Different ratios of Histoacryl and acid-treated β-TCP | | | | |
|---|---|---|---|---|
| Group | β-TCP | Histoacryl | Ratio | Weight % of β-TCP |
| composite | 0 | 1 | only Histoacryl | 0 |
|  | 4 | 1 | 4:1 | 80 |
|  | 5 | 1 | 5:1 | 83.3 |
|  | 6 | 1 | 6:1 | 85.7 |
|  | 7 | 1 | 7:1 | 87.5 |
|  | 1 | 0 | only β-TCP | 100 |

Then, Histoacryl and β-TCP coated with polymers were mixed in a weight ratio of 1:4 (75%), 1:5 (80%), 1:6 (83.3%), 1:7 (85.7%) respectively to prepare composite material.

D. Preparation of SBF

In order to examine the composite material of the present invention, a simulated body fluid (SBF) was prepared as described in Miyaji, Y et al., 1998, *J. Biomed. Mater. Res.*, 42: 604-610. NaCl, NaHCO3, KCl, K2HPO4.3H2O, MgCl2.6H2O, CaCl2 and Na2SO4 were added to 1,000 ml of secondary distilled water. Then, the final acidity was adjusted to pH 7.4 by using 1 M HCl solution and 5 mM tris(hydroxy methyl)aminomethane solution.

EXAMPLE 2

In Vitro Study

The weight of the composite material was measured in a ratio to adjust the composition in each group and mixed to prepare a sample. Then, the compressive strength, the temperature increase according to an exothermic reaction during being hardened, the cytotoxicity test for measuring the cell activity in the sample, the observation of tissue surface by using a scanning electron microscope, and X-ray diffraction (XRD) for examining a change of body fluid were conducted respectively and determined to find out the most excellent ratio. In the ratio of components, a composite material was prepared and utilized to perform an animal experiment by implanting the composite material onto rat.

(1) Compressive Strength

The sample having a size in 5 mm of height and 3 mm of radius was prepared by mixing each component in a determined ratio. After placing 24 hours under 100% of relative humidity, at 37° C., the strength was measured with a universal testing machine in 5 mm/min of cross head speed. FIG. 2 depicts the changes of compressive strengths according to combination ratios in the composite material of the present invention. As a result, it is elucidated that the strength of composite material is not changed to much extent according to the ratio, but tends to increase as the content of cyanoacrylate increases.

(2) Measurement of Exothermic Temperature During Polymerization

The composite material was mixed for 30 seconds and injected to a mold having a size in 5 mm of height and 3 mm of radius. Then, the temperature changes was measured in 3 samples per each group by inserting a thermocouple and read with a thermocouple reader (Yocogawa, Japan).

Figure 3:
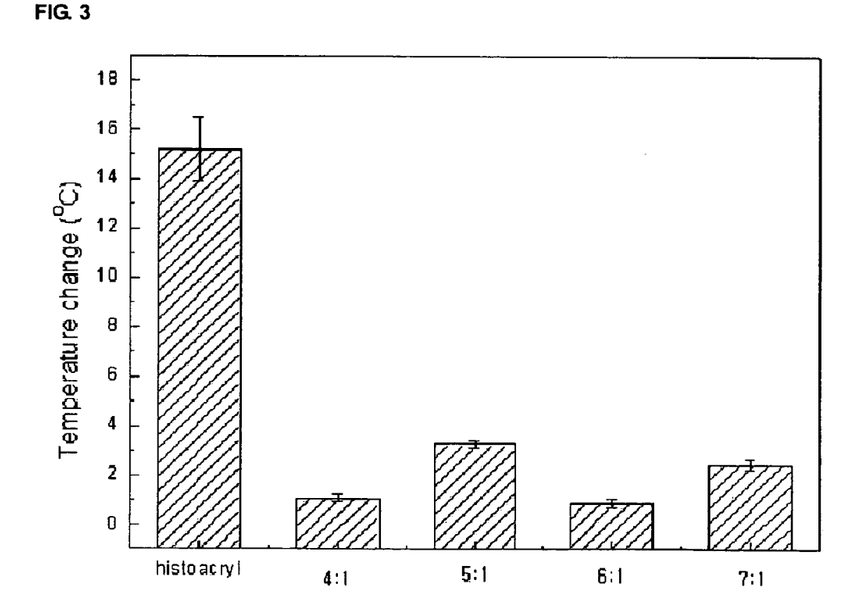
FIG. 3 depicts the exothermic temperature during the polymerization according to combination ratios in the composite material of the present invention.

FIG. 3 depicts the temperature changes during polymerizing according to combination ratios in the composite material of the present invention. As a result, it is verified that BCA is excessively exothermic while polymerizing and composites with acid-treated β-TCP slightly increases temperature.

(3) Cytotoxicity Test

In order to examine the cytotoxicity, agar overlay test was conducted by using L929 cells. For comparative groups, positive, negative, β-TCP, acidic β-TCP, and Histoacryl were utilized.

(A) Preparation of Sample

The sample was prepared to have 25 mm$^2$ of contact area in 5×5×1 of width×length×thickness (mm). For a positive sample, the Gutta percha with a response rate (4/4) for dentistry was adopted and for a negative sample, a glass plate having the same size was utilized. 4 fragments of the sample were prepared and sterilized by using E. O. gas before experiment.

(B) Experimental Procedure

L-929 cell suspension (3×10$^5$/ml) was prepared according to conventional method, injected into 90 mm petri dishes and cultivated for 24 hours. When the cells were observed to become mono-layered, culture broth was discarded from all the petri dishes and replenished with 10 ml of RPMI-agar medium at 45~50° C. Then, the resulting cells was left at room temperature for 30 minutes, dropped slowly with 10 ml of neutral red vital staining solution in the center of the solid RPMI agar medium to spread onto the surface, and left for 30 minutes. Right after removing the staining solution, the sample was adhered on the agar closely and cultivated for 24 hours at 37° C. with a 5% $CO_2$ incubator.

(C) Evaluation of Results

The resulting petri dishes were placed onto a paper to measure a de-colored area under an inverted phase contrast microscope. Then, the ratio of cell lysis was estimated within the de-colored area. The data were indicated as Zone index and Lysis index and average values were calculated in 4 samples to obtain Response index (Response index=Zone index/Lysis index)

TABLE 2

| Index | Description of zone |
|---|---|
| \multicolumn{2}{c}{Definition of index values} | |
| Zone index | |
| 0 | No detectable zone around of under sample |
| 1 | Zone limited to area under sample |
| 2 | Zone not greater than 0.5 cm in extension from sample |
| 3 | Zone not greater than 1 cm in estension from sample |
| 4 | Zone greater than 1 cm in extension from sample, but not involving entire plate |
| 5 | Zone involving entire plate |
| Lysis index | |
| 0 | No observable lysis |
| 1 | Up to 20% of zone lysed |
| 2 | 20-40% of zone lysed |
| 3 | 40-60% of zone lysed |
| 4 | 60-80% of zone lysed |
| 5 | Over 80% lysed within zone |

Table 3 illustrates the cytotoxicity measured by using agar diffusion test in bone filling materials as follows. As β-TCP increases, that is to say cyanoacrylate is lowly included, the cytotoxicity tends to decrease.

TABLE 3

| Specimens | Response index (Zone index/Lysis index) | Cytotoxicity |
|---|---|---|
| Histoacryl ® | 2/3 | Moderate |
| β-TCP | 2/2 | Mild |
| β-TCP/Histoacryl ® = 4 | 2/5 | Moderate |
| β-TCP/Histoacryl ® = 5 | 2/1 | Mild |
| β-TCP/Histoacryl ® = 6 | 1/1 | Mild |
| β-TCP/Histoacryl ® = 7 | 1/1 | Mild |
| Gutta percha (positive control) | 4/4 | Severe |
| Glass (negative control) | 0/0 | None |

Further, the composite material prepared by mixing β-TCP coated with dextrin and Histoacryl was observed to have a higher cytotoxicity than the composite material prepared by treating β-TCP with acids in the same ratio.

(4) Examination of Absorption (WSP) and Solubility (A) Deposition Test

Cyanoacrylate (Histoacryl) was mixed with β-TCP in each weight ratio and injected into a Teflon mold having a size of 10×10×1 of width×length×thickness (mm). Then, 1 kg of weight was loaded for 60 seconds and put away. In order to conduct a deposition test, the sample was injected to 10 ml of SBF solution previously made and placed at 37° C. with a 5% CO incubator for 12 weeks. At this moment, the SBF solution was replenished every week.

(B) Absorption and Solubility (a) Measurement of m1 Value

The sample was taken out of the Teflon mold and placed at 37±1° C. in a drying oven for 24 hours. Then, the resulting sample was again stored at 23±1° C. in a drying oven for an hour and weighed until not changing in more than ±0.2 mg to record m1 value.

(b) Measurement of m2 Value

The sample A was placed in SBF solution at 37±1° C. for 12 weeks and washed by using water to remove moisture completely by the naked eyes. Then, the resulting sample was left in the air for 15 seconds and weighed to record m2 value in a minute after removing water.

(c) Measurement of m3 Value

The sample B was treated again by the procedure of the sample A and weighed to record m3 value.

By using the following formulas, the absorption (WSP) and the solubility (WSL) were calculated in 5 samples respectively by $mg/mm^3$ unit.

$$WSP=(m2-m3)/v$$

$$WSL=(m1-m3)/v$$

v: volume of sample

Figure 4:
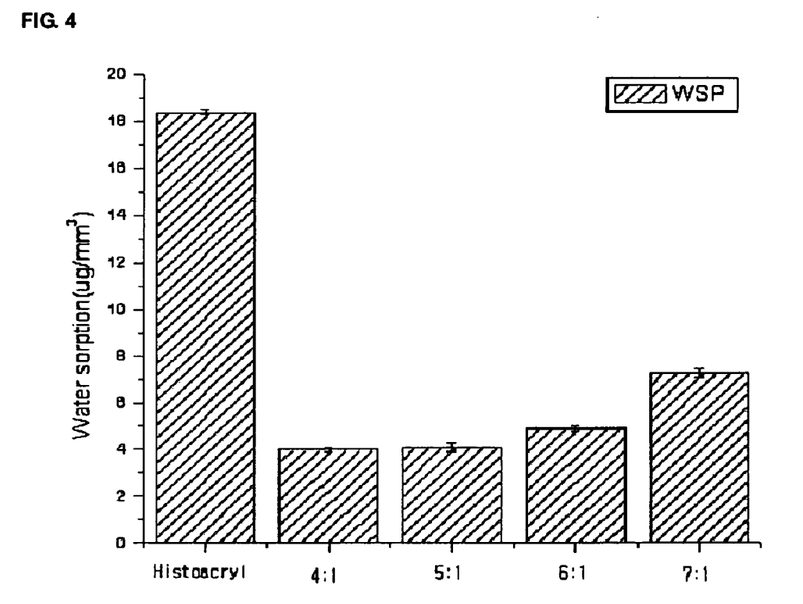
FIG. 4 depicts the absorption according to combination ratios in the composite material of the present invention.
Figure 5:
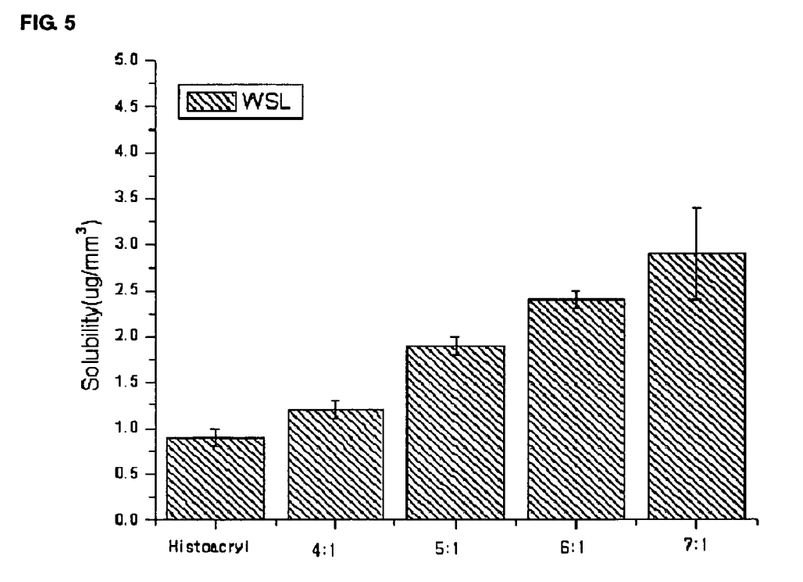
FIG. 5 depicts the solubility according to combination ratios in the composite material of the present invention.

FIG. 4 depicts the absorption of the composite material of the present invention according to combination ratios. FIG. 5 depicts the solubility of the composite material of the present invention according to combination ratios. As a result, the composite material was observed to increase the absorption and the solubility, as β-TCP mineral is more included.

(5) Observation of Surface

Figure 6:
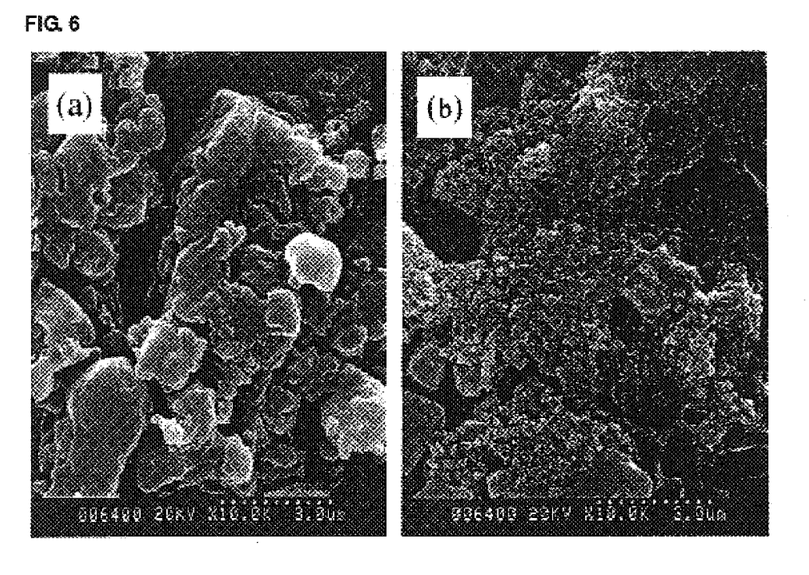
FIG. 6 depicts the surface change of composite material (5:1) before (a) depositing and after (b) SBF depositing for 4 weeks.

The sample was manufactured and deposited in SBF solution for 12 weeks and dried to observe the change of surface morphology. Cyanoacrylate-β-TCP composite was examined by performing a scanning electron microscopy (SEM; S2700, Hitachi, Japan). As a result, its surface became coarse after deposited in SBF for 12 weeks. Thus, the surface is elucidated to enable cells proliferate and bones regenerated, since attaching cells easily. FIG. 6 depicts the surface change of composite material before (a) depositing and after (b) SBF depositing for 4 weeks.

(6) XRD Examination

The sample was manufactured, deposited in SBF solution and stored for 12 weeks. For a comparative group, glass plate and glass plate treated with Histoacryl on the surface were utilized. In order to identify the product formed on the surface, the sample was examined by conducting XRD analysis. In detail, the resultant produced on the surface of cyanoacrylate-β-TCP composite after deposited for 12 weeks was identified by conducting XRD analysis. At this moment, XRD instrument (XRD, D-Max Rint240 Model, Rigaku, Japan) was utilized under the following condition: Target: CuKα, Scanning speed: 4₀/min, Filter: Ni, Full scale: 400 cps, Powder: 30 kV/30 mA.

Figure 7:
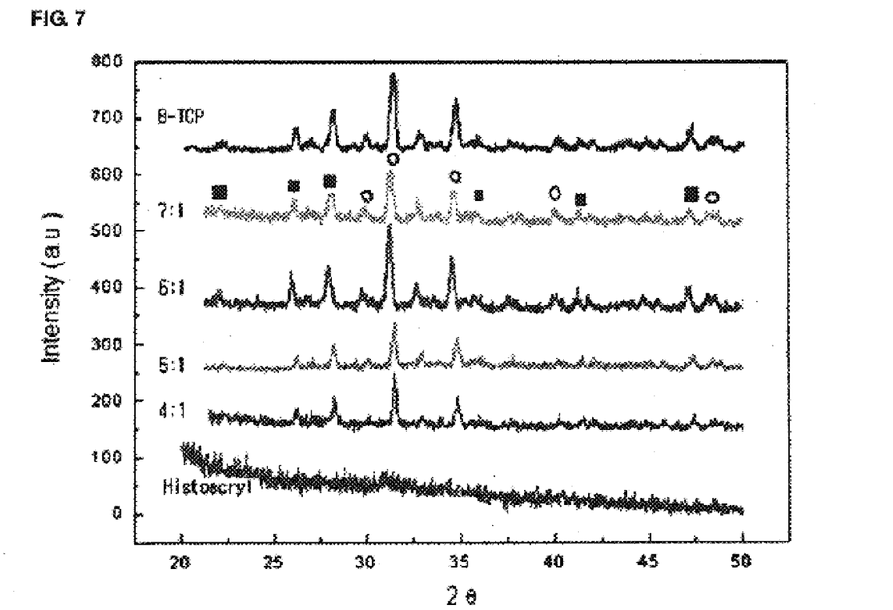
FIG. 7 depicts the X-ray diffraction pattern of the composite material after SBF depositing for 12 weeks.

FIG. 7 depicts the X-ray diffraction pattern of the composite material after SBF depositing for 12 weeks. ■ and ○ are diffraction lines corresponding to HA and β-TCP respectively. As a result, the reactant observed on the surface of β-TCP under a SEM, was proved to be HA by the XRD analysis.

EXAMPLE 3

In Vivo Study 13 males of Spraque-Dawley rats having 200~300 g of body weight were divided into 4 rats of comparative group, 6 rats of experimental group implanted with material and 3 rats of augmentation group and utilized for the experiment (See Table 4).

TABLE 4

Summary of experiment design

| Group | No of rat | Duralion of Implantation (weeks) |
|---|---|---|
| Autograft | 2 | 8.16 |
| Control Positive (Only hall defect) | 1 | 16 |
| Control Negative (No hall defect) | 1 | 8 |
| Cynoacrylate-β-TCP powdered sample | 3 | 8.16 |
| Cynoacrylate-β-TCP Dense sample | 3 | 8.16 |
| Cynoacrylate-β-TCP Augmentation | 3 | 8.16 |

(1) Management and Operation of Animals (A) Selection and Bleeding of Animal

The experimental animals were provided with sterilized fodder and water at 21° C. for 6 weeks to be adapted in a laboratory. The animals were bred according to the instruction of the breeding laboratory in Department of dentistry, Yonsei University.

(B) Anesthesia of Animal

General narcotherapy was conducted to anesthetize animals. In detail, ketamine hydrochloride and rumphun were mixed in a ratio of 5:1 and injected intramuscularly (5 mg/kg) to anesthetize whole body. Then, surgical lesion was anesthetized locally (2% lidocaine, 1:100,000 epi).

(c) Operation

Figure 8:
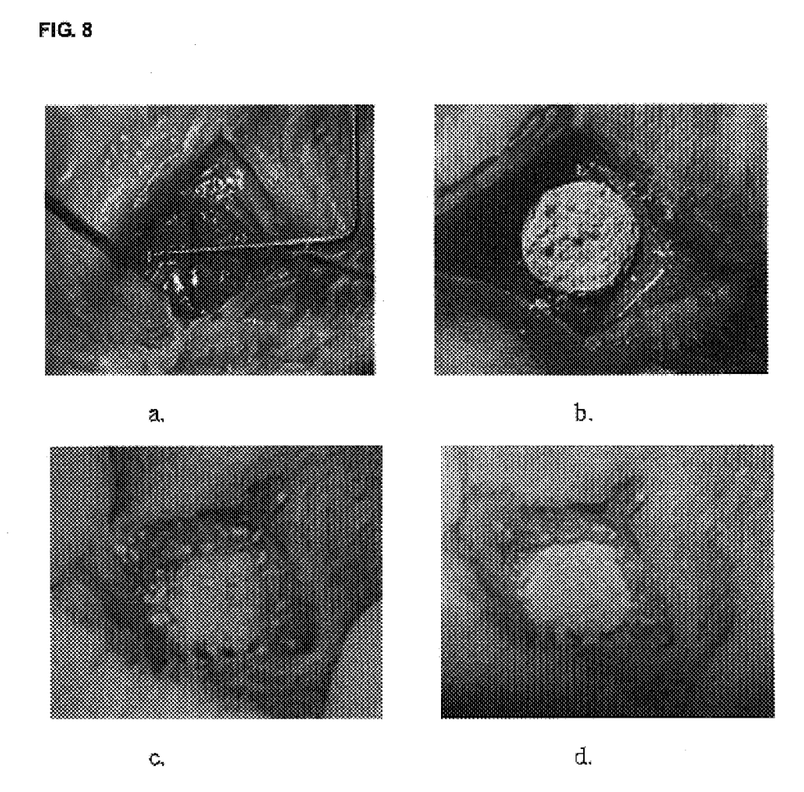
FIG. 8 depicts the operation of experimental rats by using the composite material of the present invention in Examples.

The surgical site was treated to remove hairs with a mechanical remover and disinfected by using iodine. Cranial bone was cut in about 3 cm of size perpendicularly to a sagittal plane with a surgical knife. Then, its cuticle was turned inside out toward periosteum to expose calvarial bone. FIG. 8 depicts the operation of experimental rat by using the composite material of the present invention.

(2) Implantation Study

The frontal region exposed on rat was injured in more than critical size with 8 mm radius by using a round bar and then, cooled by using physiological saline solution in order to prevent necrosis.

(A) Comparative Group

Above all, the lesion site was washed by using physiological saline solution without any manipulation. In the autograft group, the autogenic bone brought out was sonicated, placed on the lesion and sealed with 3-0 black silk.

(B) Experimental Group

The experimental group was divided to 2 kinds and examined. The first group of 3 rats was filled on the lesion with a composite material (cyanoacrylate: β-TCP=1:5) right after mixing. The other group of 3 rats was treated on the lesion with a composite material after preparing a disk with 8 mm radius of Teflon mold. The experimental rats were disinfected the next day of the operation and manipulated to remove a sealing thread after 1 week.

(C) Observation

The resulting rats were sacrificed after 8 weeks and 16 weeks respectively and measured on defects ad follows.

(a) Observation by Naked Eyes

Figure 9:
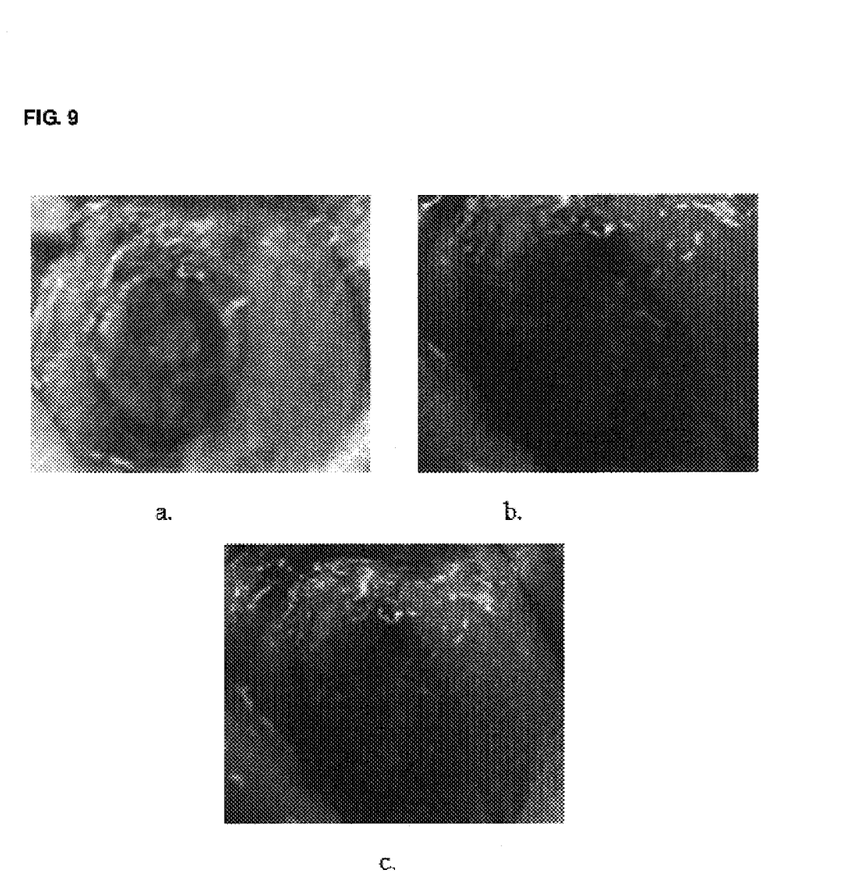
FIG. 9 depicts the observation of the composite material of the present invention by the naked eyes after 8 weeks.

The bone composite remained was examined whether recovering a skeletal contour or not. After 8 weeks, the experimental group was observed by the naked eyes to maintain the position and morphology without any change, compared to those during the operation (See FIGS. 9a and 9b). FIG. 9 depicts the observation of the composite material of the present invention by the naked eyes after 8 weeks: (a) dense disk; (b) direct filling; and (c) augmentation.

Figure 10:
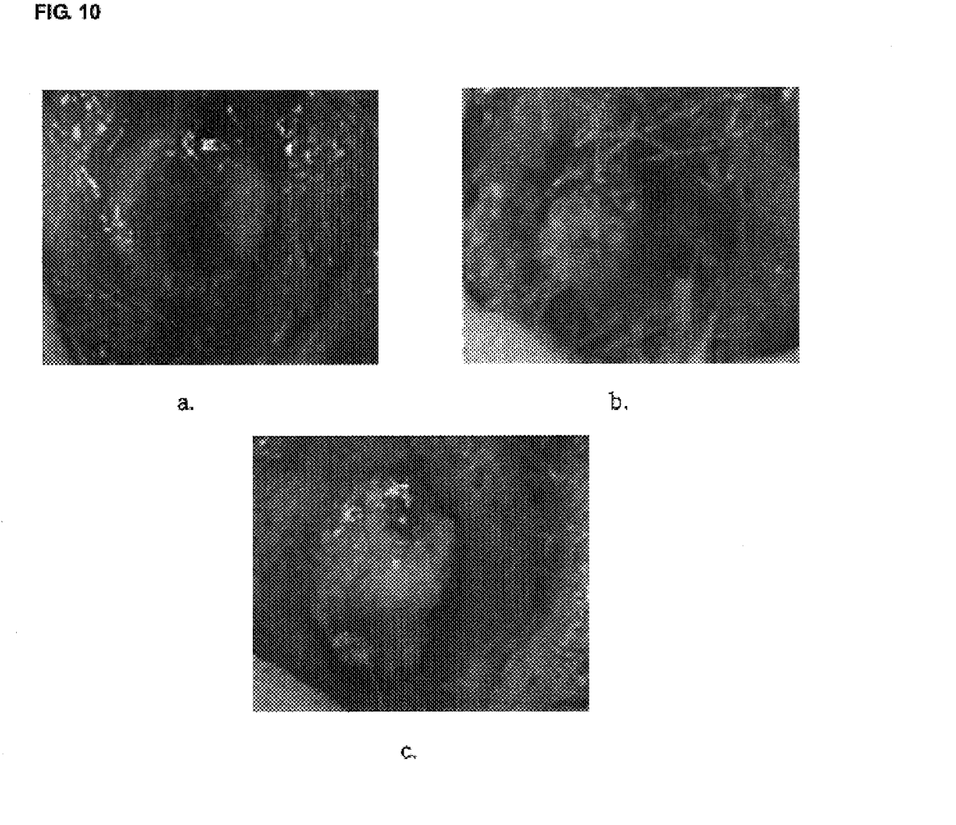
FIG. 10 depicts the observation of the composite material of the present invention by the naked eyes after 16 weeks.

As a result, it was observed by the naked eyes in 16 weeks that the control group treating no manipulation after injured maintained the lesion without any sense by conducting a palpation. The experimental groups were observed to become similar to the appearance during the operation and after 8 weeks. But, the composite material appeared to be integrated into the bone and was seldom changed in its position and morphology (FIGS. 10a and 10b). FIG. 10 depicts the observation of the composite material of the present invention by the naked eyes after 16 weeks: (a) dense disk; (b) direct filling; and (c) augmentation.

(b) Histological Observation

The lesion site was cut out minimally in more than 10 mm of size, then decalcified for 7 days, and implanted on paraffin. The resulting coronal was taken out in 3 μm of thickness and stained by using hematoxylineosin (H-E stain). After that, the composite material and adjacent tissues were observed to examine whether inflammatory cells proliferate or not and whether new bone is formed or not.

Figure 11:
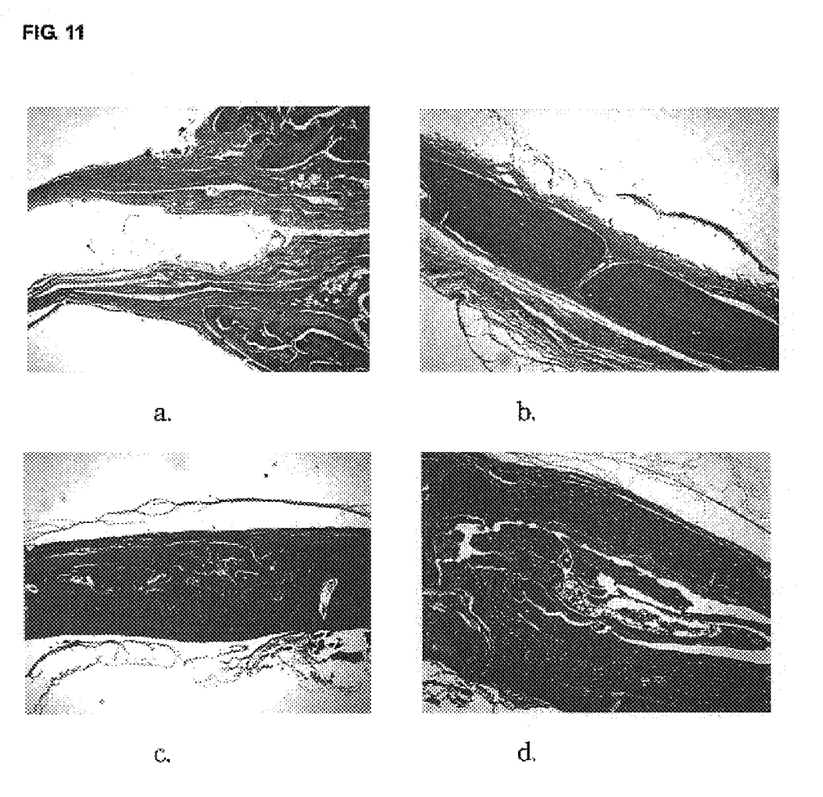
FIG. 11 depicts the histological examination of the control group by performing a microscopy.

As a result, the control group without any manipulation was observed to fill the lesion site with a connective tissue even after 16 weeks (See FIG. 11a). The experimental group implanting an autograft is observed to have both connective tissue and new bone around the autograft (See FIG. 11b), but almost fill with new bone after 16 weeks (See FIGS. 11c and 11d). FIG. 11 depicts the histological examination of the control group by performing a microscopy: (a) control after 16 weeks later; (b) autograft after 8 weeks later; (c) autograft after 16 weeks later (×50); and (d) autograft after 16 weeks later (×100).

Figure 12:
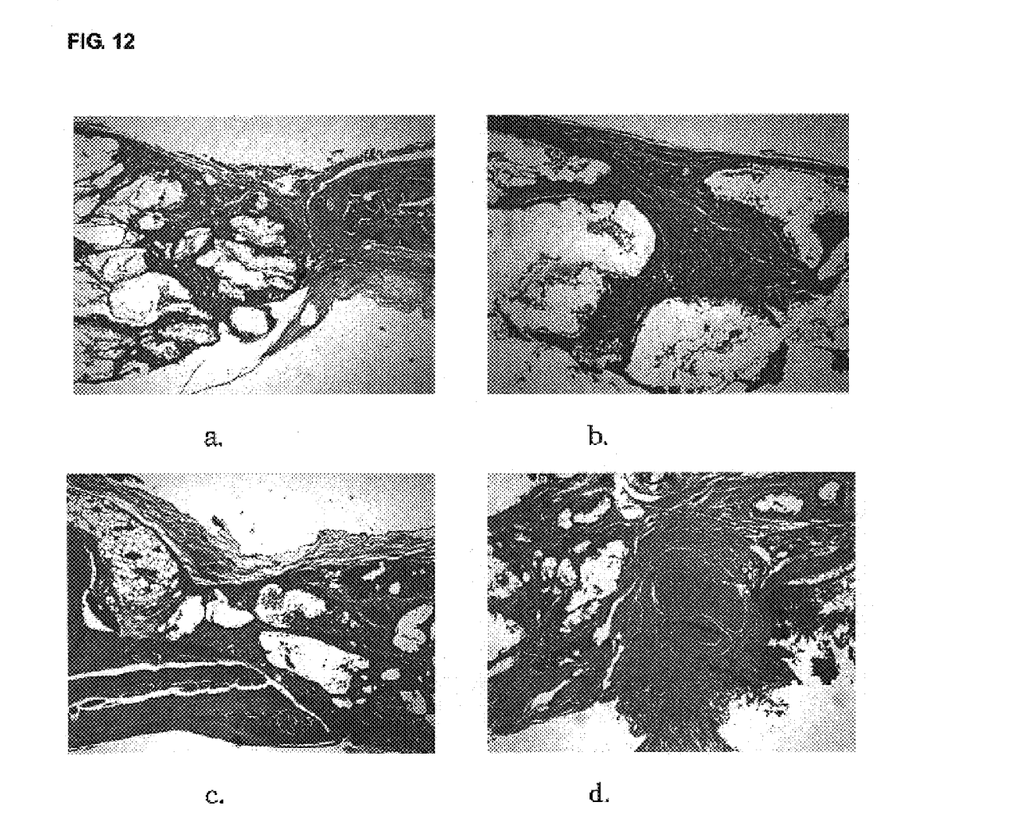
FIG. 12 depicts the histological examination of the experimental group that directly filled the composite material of the present invention, by performing a microscopy.

The experimental group filling the composite material directly onto a lesion was observed to include both connective tissue and new bone around the material even after 8 weeks and is not discriminated from the autograft group. The lesion site vacant or degrading BCA was filled with connective tissues (See FIGS. 12a and 12b). After 16 weeks, the resulting tissue was observed to regenerate the bone tissue almost completely (See FIGS. 12c and 12d). FIG. 12 depicts the histological examination of the experimental group that directly fills the composite material of the present invention by performing a microscopy: (a) after 8 weeks later (×50); (b) after 8 weeks later (×100); (c) after 16 weeks later (×50); and (d) after 16 weeks later (×100).

Figure 13:
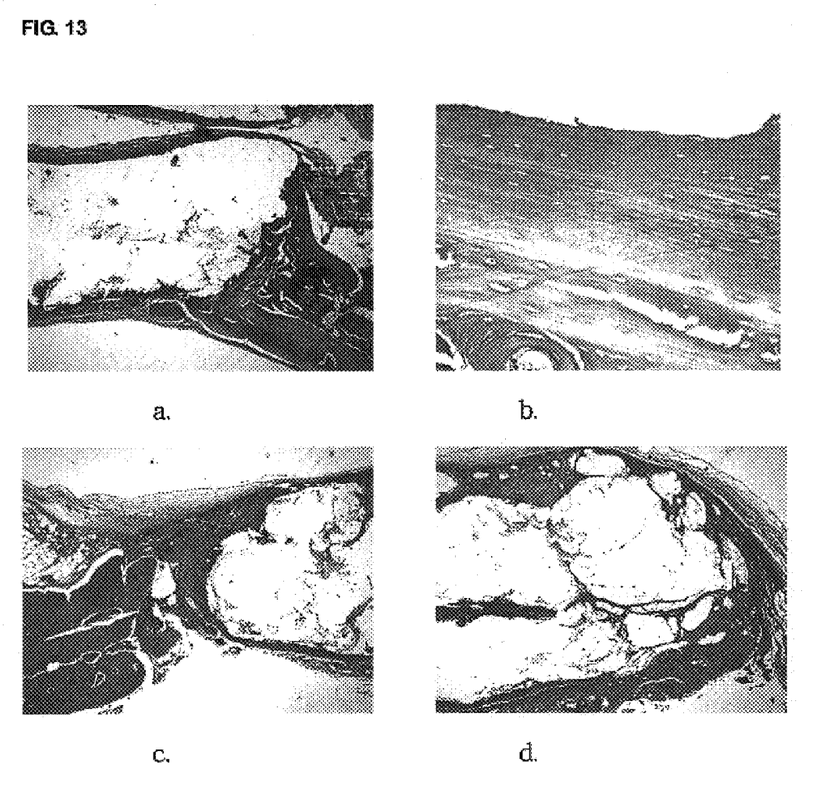
FIG. 13 depicts the histological examination of the experimental group that is treated by using the round plate-type implant of the composite material of the present invention, by performing a microscopy.

The experimental group treating a round plate type implant was observed to maintain a composite material after both 8 and 16 weeks without ay change and make new bone over and beneath the implant (See FIGS. 13a and 13b). The round plate type implant changed its appearance even in 16 weeks and replaced for the composite material by bones, as time lapsed (See FIGS. 13c and 13d). FIG. 13 depicts the histological examination of the experimental group that is treated by using the round plate type implant of the composite material of the present invention by performing a microscopy: (a) after 8 weeks later (×50); (b) top portion after 8 weeks later (×400); (c) after 16 weeks later (×50); and (d) after 16 weeks later (×100).

(3) Augmentation Study

Calvarial bone was exposed by conducting a dull thickness flap and made to a projection having a size in 8 mm of radius and 2 mm of height by mixing a composite material. Then, the lesion was sealed with 3-0 black silk and unsealed after 1 week. The experimental rats were victimized after 8 and 16 weeks respectively and examined onto the augmentation site by the change of material as follows.

(A) Observation by the Naked Eyes

Above all, the experimental rats were examined whether the lesion maintained the shape of augmentation or not and whether it moved during the palpation or not. As a result, the augment group was observed after 8 weeks by the naked eyes to maintain the implant without movement as the implant group did (See FIG. 9c). Then, it was observed by the naked eyes that the augment group attached onto bone closely and did not move during palpation. Further, the lesion site appeared not to change in size even after 16 weeks (See FIG. 10c).

(B) Histological Observation

The attachment site was examined histologically whether it formed gaps or not and whether new bone or soft tissue penetrated between the gaps by performing the same procedure described in the experimental group of bone defect. As a result, it was observed that the attachment was so close onto bone not to move during palpation and appeared not to change in size even after 16 weeks.

Figure 14:
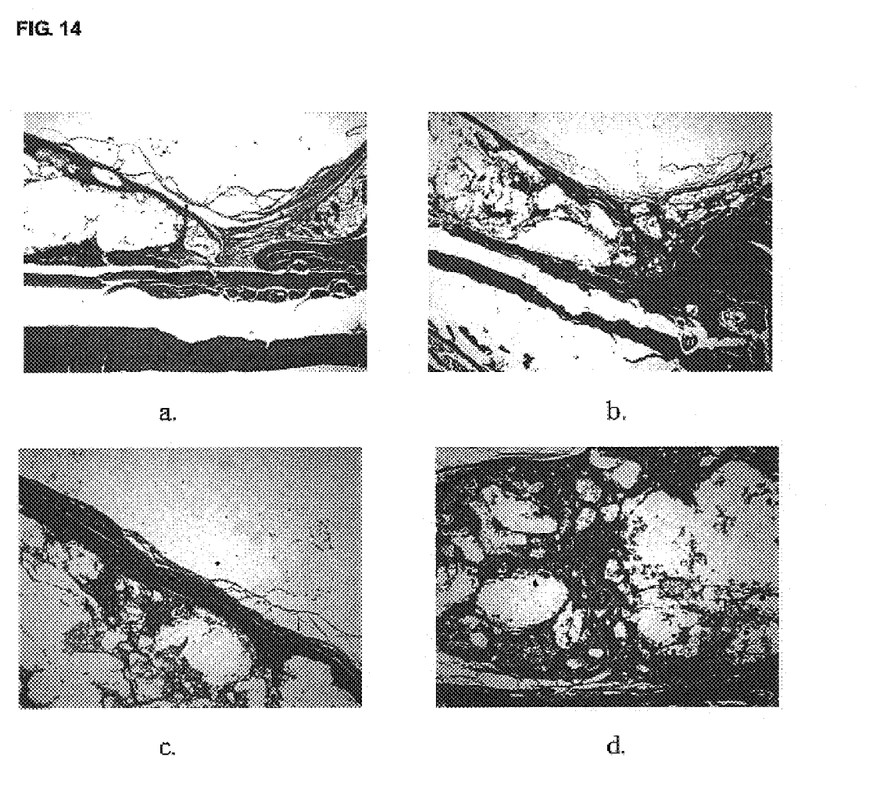
FIG. 14 depicts the histological examination of the composite material of the present invention after augmented, by performing a microscopy.

In a histological opinion, the attachment site absorbed composite material and was filled with new bone in a shallow portion after 8 weeks (See FIG. 14a). After 16 weeks, this site was covered with new bone and permeated by the new bone, if partially filled or dissolved (See FIGS. 14b, 14c and 14d). FIG. 14 depicts the histological examination of the composite material of the present invention after augmented by performing a microscopy: (a) after 8 weeks later (×50); (b) after 16 weeks later (×50); (c) top portion after 16 weeks later (×50); and (d) middle portion after 16 weeks later (×100).

Consequently in the present invention, the composite material for bone replacement comprising biodegradable organic material, Histoacryl made of n-butyl-2-cyanoacrylate (BCA) as a main component; and biodegradable inorganic material, β-TCP encapsulated with acids such as citric acid or dextrin is manufactured and investigated to obtain the experimental data as follows.

1. In the composite material of BCA and β-TCP, the compressive strength increases, as the amount of BCA increases.

2. In the composite material, the exothermic energy generated during the polymerization decreases, compared to pure BCA.

3. The cytotoxicity decreases, as BCA is less and β-TCP is more added.

4. The degree of absorption and the solubility increase, as β-TCP, an additive increases.

5. The composite material is examined to become rough on the surface after precipitated in SBF for 12 weeks by SEM observation.

6. The precipitate produced in SBF on the surface after 12 weeks is identified to be hydroxyapatite by XRD test.

7. The cranial bone (8 mm of radius) of experimental animal deleted in a more than critical size regenerates new bones in between the lesion and implant material, when the composite material is implanted.

Therefore, it is confirmed that the composite material for bone replacement that combines organic material as a substrate and osteo-conductive inorganic material as an additive can be synthesized.

As illustrated and confirmed above, the composite materials according to the present invention, maximize the merits of organic material and inorganic material and minimizes their demerits. In detail, the organic material has the maintenance of shape and the adhesive property and the inorganic material has the osteo-conductivity on new bones. Therefore, the composite materials of the present invention can be applied to fill bone defect and replace, since they retain the excellent physical property.

Those skilled in the art will appreciate. that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A composite material for bone defect filling and bone replacement which combines organic material and inorganic material, wherein the organic material is cyanoacrylate and the inorganic material is calcium phosphate modified on the surface by using an inhibitor against the polymerization of the organic material.

2. The composite material for bone defect filling and bone replacement according to claim 1, wherein the cyanoacrylate is n-butyl-2-cyanoacrylate.

3. The composite material for bone defect filling and bone replacement according to claim 1, wherein the calcium phosphate is β-tricalcium phosphate (β-TCP).

4. The composite material for bone defect filling and bone replacement according to claim 1, wherein the calcium phosphate is modified on the surface by encapsulating with acids or polymers.

5. The composite material for bone defect filling and bone replacement according to claim 4, wherein the polymers are bio-degradable polymers.

6. The composite material for bone defect filling and bone replacement according to claim 1, wherein the cyanoacrylate and the calcium phosphate are combined in a ratio of 1:4 to 1:7.

* * * * *